(12) United States Patent
Siegel et al.

(10) Patent No.: US 10,894,780 B1
(45) Date of Patent: Jan. 19, 2021

(54) CONVERSION OF Δ9-THC TO Δ10-THC

(71) Applicants: Alexander William Siegel, Albany, CA (US); Alek Enrique Valle, Novato, CA (US); Devin Jay Wall, Vallejo, CA (US)

(72) Inventors: Alexander William Siegel, Albany, CA (US); Alek Enrique Valle, Novato, CA (US); Devin Jay Wall, Vallejo, CA (US)

( * ) Notice: Subject to any disclaimer, the term of this patent is extended or adjusted under 35 U.S.C. 154(b) by 0 days.

(21) Appl. No.: 16/715,368

(22) Filed: Dec. 16, 2019

(51) Int. Cl.
*C07D 311/80* (2006.01)

(52) U.S. Cl.
CPC .................. *C07D 311/80* (2013.01)

(58) Field of Classification Search
CPC .................................................. C07D 311/80
See application file for complete search history.

(56) References Cited

PUBLICATIONS

Srebnik, M., "Base-catalysed double-bond isomerizations of cannabinoids: structural and stereochemical aspects." Journal of the Chemical Society, Perkin Transactions 1 (1984): 2881-2886.*
WHO Expert Committee on Drug Dependence Critical Review—Isomers of THC—World Health Organization (2018):1-48.*

* cited by examiner

*Primary Examiner* — John M Mauro
(74) *Attorney, Agent, or Firm* — Brubaker Law Group PLLC

(57) ABSTRACT

Methods of converting Δ9-THC to Δ10-THC are described and the products disclosed. The methods do not affect existing CBD or CBG in the extract. Various adjustments can be made to the reactions resulting in increased or decreased product and by-product.

19 Claims, 1 Drawing Sheet

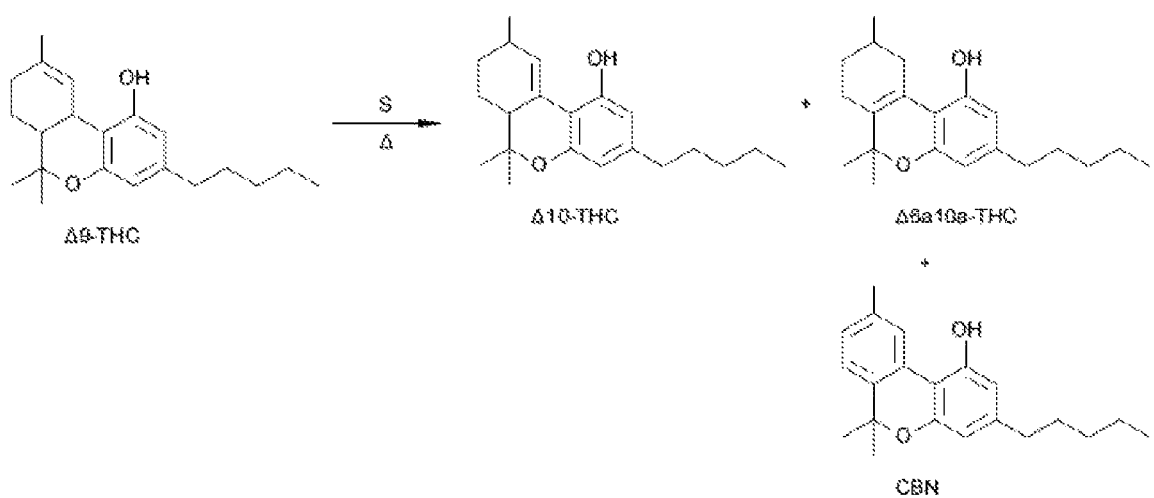

CONVERSION OF Δ9-THC TO Δ10-THC

TECHNICAL FIELD

The present invention relates to the chemical synthesis of an extract of *cannabis*. More specifically, the present invention relates to converting Δ9-THC into Δ10-THC and with minor products Δ6a10a-THC and CBN.

BACKGROUND

Public interest in *Cannabis* as medicine is well-established, based in no small part on the fact that *Cannabis* has long been considered to have medicinal properties, ranging from treatment of cramps, migraines, convulsions, appetite stimulation and attenuation of nausea and vomiting. In fact, a report issued by the National Academy of Sciences' Institute of Medicine indicated that the active components of *Cannabis* appear to be useful in treating pain, nausea, AIDS-related weight loss, muscle spasms in multiple sclerosis as well as other problems. Advocates of medical marijuana argue that it is also useful for glaucoma, Parkinson's disease, Huntington's disease, migraines, epilepsy and Alzheimer's disease.

Δ10-THC: In the literature is reported a synthesis of the two stereoisomers obtained by base catalyzed isomerization of (−)-trans-Δ9-THC by Srebnik in 1984. Treatment of (−)-trans-Δ9-THC with base gave a mixture of (6aR-trans)-Δ10-THC (m.p. 153-154° C.; α−133°) and (6aR-cis)-Δ10-THC (m.p. 54-55° C.; α−70°), that are further separated by chromatography. Δ10-THC has no reported psychoactivity, is stable in solution, and may be a viable non-psychoactive therapeutic compound. Δ10-THC may be a viable "cutting" agent, which can thicken and dilute *cannabis* or hemp extract without adding psychoactivity or other physical effects. Use of Δ10-THC as a cutting agent for CBD products may also be viable as Δ10-THC is not currently identified by any known state or federal testing hemp laboratory. Invention does not degrade or change CBD or CBG and can thus be used to 'remediate' Δ9-THC from CBD or CBG products.

Δ6a10a-THC: Δ6a10a-THC is not a naturally occurring cannabinoid and is generally obtained by chemical synthesis. The condensation between olivetol and pulegone under acid catalysis for the preparation of Δ6a10a-THC in its racemic form was investigated in the early 1940s. The synthesis and isolation of (R)-(+)-Δ6a10a-THC and (S)-(−)-Δ6a10a-THC was achieved in 1984. The method used the single enantiomers of Δ10-THC1, (9R,6aR)-Δ10-THC and (9S,6aR)-Δ10-THC, as starting material that isomerized in toluene-p-sulphonic acid in benzene to lead to (R)-(+)-Δ6a10a-THC and (S)-(−)-Δ6a10a-THC, respectively. More recently, Rosati et al. developed a one-pot microwave assisted synthesis of (R)-(+)-Δ6a10a-THC and (S)-(−)-Δ6a10a-THC starting from single enantiomers of pulegone condensed with olivetol under Ytterbium triflate-ascorbic acid catalysis. Δ6a10a-THC may be a viable "cutting" agent, which can thicken and dilute concentrated *cannabis* or hemp extract without adding psychoactivity or other ill physical effects. Use of Δ6a10a-THC as a cutting agent for CBD products may also be viable as Δ6a10a-THC is not currently identified by any known state or federal testing hemp laboratory. Under certain conditions, invention does not degrade or change CBD or CBG and can thus be used to 'remediate' Δ9-THC from CBD or CBG products.

Clearly, as the cannabinoids are of potential medicinal value, improved methods of converting Δ9-THC to Δ10-THC, Δ6a10a-THC, and CBN are needed.

SUMMARY OF THE INVENTION

A method and product are disclosed for converting Δ9-THC to Δ10-THC, Δ6a10a-THC, and CBN comprising:
1. Adding a catalyst to Δ9-THC at a Δ9-THC to catalyst ratio of at least 1000 moles to 1 mole, and
2. Heating the reaction above 130° C.

The varying the heat, catalyst to THC ratio, and the atmospheric conditions results in the acceleration or deceleration of general and/or side reactions.

BRIEF DESCRIPTION OF DRAWINGS

The FIGURE shows the chemical formula of the general reaction.

DETAILED DESCRIPTION

In the Summary above and in this Detailed Description, and the claims below, and in the accompanying drawings, reference is made to particular features of the invention. It is to be understood that the disclosure of the invention in this specification includes all possible combinations of such particular features. For example, where a particular feature is disclosed in the context of a particular aspect or embodiment of the invention, or a particular claim, that feature can also be used—to the extent possible—in combination with and/or in the context of other particular aspects and embodiments of the invention, and in the invention generally The term "comprises" and grammatical equivalents thereof are used herein to mean that other components, ingredients, steps, etc. are optionally present. For example, an article "comprising" (or "which comprises") components A, B, and C can consist of (i.e., contain only) components A, B, and C, or can contain not only components A, B, and C but also contain one or more other components.

Where reference is made herein to a method comprising two or more defined steps, the defined steps can be carried out in any order or simultaneously (except where the context excludes that possibility), and the method can include one or more other steps which are carried out before any of the defined steps, between two of the defined steps, or after all the defined steps (except where the context excludes that possibility).

The term "at least" followed by a number is used herein to denote the start of a range including that number (which may be a range having an upper limit or no upper limit, depending on the variable being defined). For example, "at least 1" means 1 or more than 1. The term "at most" followed by a number is used herein to denote the end of a range, including that number (which may be a range having 1 or 0 as its lower limit, or a range having no lower limit, depending upon the variable being defined). For example, "at most 4" means 4 or less than 4, and "at most 40%" means 40% or less than 40%. When, in this specification, a range is given as "(a first number) to (a second number)" or "(a first number)-(a second number)," this means a range whose limits include both numbers. For example, "25 to 100" means a range whose lower limit is 25 and upper limit is 100, and includes both 25 and 100.

Described herein are methods and protocols for converting Δ9-tetrahydrocannabinol (Δ9-THC) to Δ10-tetrahydrocannabinol (Δ10-THC). Described herein are also methods and protocols for converting Δ9-THC to Δ10-THC, Δ6a10a-tetrahydrocannabinol (Δ6a10a-THC), and cannabinol (CBN). As will be appreciated by one knowledgeable in the art and as discussed below, the reaction times may be varied somewhat, producing product at different yields and purities. Furthermore, functional equivalents may be substituted where appropriate.

Specifically, described herein is a method of converting Δ9-THC to another THC and/or cannabinol comprising: a reaction mixture comprising Δ9-THC, heating and mixing said reaction mixture, adding catalyst to reaction mixture, allowing the mixture to cool; and then, in some embodiments, purifying reaction products. The THC may then be combined with suitable excipients known in the art, thereby forming a pharmaceutical composition.

In most embodiments, the catalyst may be a Lewis base, such as elemental sulfur.

In some embodiments, the catalyst may be added at a ratio of 21.0 g Δ9-THC to 0.20 g sulfur. In other embodiments, sulfur may be added at a higher ratio, for example 21 g Δ9-THC to 2.0 g sulfur. In other embodiments insufficient catalyst may be added, for example 21 g Δ9-THC to 0.04 g sulfur.

In some embodiments the temperature may be held constant at 130° C. In other embodiments the temperature may be raised or held constant at higher temperatures. Temperatures above 200° C. are shown to decrease concentration of Δ6a10a-THC via degradation into currently unknown cannabinoids.

In some embodiments the process may be carried out under atmospheric conditions. In other embodiments the process may be carried out under vacuum. In other embodiments the process may be carried out under inert conditions.

Yield may be determined by looking at the peak area for the isolated compound in the liquid chromatography—PDA analysis of the crude reaction product mixture.

Purity may also be determined by looking at the peak area for the isolated compound in the liquid chromatography—PDA analysis of the crude reaction product mixture.

As discussed below, in some embodiments, purity of the Δ10-THC isolated by the process may be greater than 90% after purification. In some embodiments, purity of the Δ10-THC may be less than 1%.

According to one of the invention, a method is provided of converting Δ9-THC to Δ10-THC. According to another aspect of the invention, a method is provided of converting Δ9-THC to a mixture of Δ10-THC and Δ6a10a-THC. According to another aspect of the invention, a method is provided of converting any concentration of Δ9-THC to Δ10-THC, Δ6a10a-THC, and CBN. According to another aspect of the invention, a method is provided of converting Δ9-THC in low concentrations (less than 10%) to low concentration Δ10-THC, Δ6a10a-THC, and CBN.

Some aspects consist of adding Δ 9-THC in a reaction mixture; mixing the reaction mixture; heating the reaction mixture while mixing, adding catalyst, heating for a period of time; and allowing the reaction mixture to cool. Reactions that may be considered are listed below:

1. General Reaction 1: Δ9-THC+S (catalyst)+Δ→Δ10-THC
2. General Reaction 2: Δ10-THC+S (catalyst)+Δ→Δ6a10a-THC
3. Side Reaction 1: Δ9-THC+$O_2$+Δ→CBN+2 $H_2O$
4. Side Reaction 2: Δ10-THC+$O_2$+Δ→CBN+2 $H_2O$
5. Side Reaction 3: Δ6a10a-THC+$O_2$+Δ→CBN+2 $H_2O$
6. Side Reaction 4: Δ9-THC+2S+Δ→CBN+2 $H_2S$
7. Side Reaction 5: Δ10-THC+2S+Δ→CBN+2 $H_2S$
8. Side Reaction 6: Δ10a6a-THC+2S+Δ→CBN+2 $H_2S$
9. Side Reaction 7: Δ9-THC+Δ→CBN+2$H_2$
10. Side Reaction 8: Δ9-THC+Δ+$H^+$→Δ8-THC+$H^+$ It is noted that when concentration of Δ9-THC is decreased, all reaction rates decrease except for General Reaction 2, Side Reaction 2, Side Reaction 3, Side Reaction 5, and Side Reaction 6. When temperature is increased all reactions increase in rate.

EXAMPLES

Example 1: Conversion of Δ9-THC to Δ10-THC, Δ6a10a-THC, and CBN Using Sulfur (Notebook B02-5)

The first example displays the General Reaction 1 and General Reaction 2 along with Side Reaction 1, 2, 3, 4, 5, and 6 taking place, although Side Reactions 4, 5, and 6 are minimized through use of small amounts of sulfur, which encourages sulfur to function as a catalyst rather than a reagent. A ratio of 22 grams of THC-rich oil (87.0% pure, 19.14 g Δ9-THC, 61.0 mmol Δ9-THC) to 0.202 g (6.25 mmol) elemental sulfur pellets was used, although Δ9-THC concentration and catalyst concentration may vary. In this example, catalyst was added at room temperature and the mixture temperature was increased to 220° C. under atmospheric conditions. Heat was maintained at 220° C. under atmosphere for 40 minutes. After 10 minutes under heat, during which mixture temperature increased to 190° C., Δ9-THC concentration reduced to 37.8% with generation of 21.8% Δ10-THC, 17.5% Δ6a10a-THC, and 7.4% CBN. After 10 more minutes, temperature reached 220° C. and Δ9-THC concentration had reduced to 4.5% with generation of 38% Δ10-THC 23%, Δ6a10a-THC, and 18.8% CBN. After 20 minutes at 220° C., Δ9-THC concentration reduced to 1.2% with generation of 33% Δ10-THC, 15% Δ6a10a-THC, and 28% CBN. After 40 minutes at 220° C., Δ9-THC concentration reduced to 0.53% with generation of 26% Δ10-THC, 7.2% Δ6a10a-THC, and 33% CBN. After 40 minutes at 220° C., multiple new significant peaks account for up to 5% lost mass which may be quantified as other cannabinoids in later work.

Example 2: Conversion of Δ9-THC to Δ10-THC, Δ6a10a-THC Using Sulfur, Maximizing Δ6a10a-THC The second example displays the General Reaction 1 and General Reaction 2 under atmospheric conditions and lower temperature (185° C.) to minimize Side Reactions 1, 2, and 3 which generate excess CBN. Lower temperatures than in Example 1 and minimal sulfur were used in order to minimize Side Reactions 4, 5, and 6, which reduce concentration of Δ10-THC and Δ6a10a-THC. Lower temperatures were also used in order to decrease the rate of degradation of Δ6a10a-THC into CBN. A ratio of 22 grams of THC-rich oil (87.0% initial concentration) to 0.202 g (6.25 mmol) elemental sulfur pellets was used although Δ9-THC concentration and catalyst concentration may vary. In this example, catalyst was added first and the mixture was heated to 185° C. under atmospheric conditions. The mixture was then heated for 20 minutes. After 20 minutes at 185° C., Δ9-THC concentration reduced to 10.5% with generation of 34.7% Δ10-THC, 26.2% Δ6a10a-THC, and 14.8% CBN. The mixture was then cooled under nitrogen to prevent degradation of Δ6a10a-THC to CBN. Reversed-phase chromatography or distillation may be used to further purify Δ6a10a-THC.

Example 3: Conversion of High Purity Δ9-THC to Δ10-THC Using Sulfur

The third example displays the General Reaction 1 and General Reaction 2 and uses nitrogen to minimize Side Reactions 1, 2, and 3 which generate excess CBN. Additionally, minimal sulfur was used in order to minimize Side Reactions 4, 5, and 6, which reduce concentration of Δ10-THC and Δ6a10a-THC. A higher temperature than Example 2 was used in order to increase the rate of General Reaction 1, generating a higher concentration of A 10-THC, although Δ6a10a-THC may decrease due to degradation. A ratio of 22 grams of Δ9-THC (initially 25 gs of Δ9-THCa, 93.2% initial concentration) to 0.204 g elemental sulfur pellets was used although Δ9-THC concentration and catalyst concentration may vary. In this example, the mixture was heated to 200° C. under nitrogen and then catalyst was added. The mixture was heated under nitrogen for 1 hour. 5 minutes after the catalyst was introduced at 200° C., Δ9-THC concentration reduced to 41.3% with generation of 27.8% Δ10-THC, 20.7% Δ6a10a-THC, 4.20% CBN, and 0.7% Δ8-THC. 10 minutes after the catalyst was introduced at 200° C., Δ9-THC concentration reduced to 30.7% with generation of 34.8% Δ10-THC, 25.1% Δ6a10a-THC, 4.50% CBN, and 0.8% Δ8-THC. 20 minutes after the catalyst was introduced at 200° C., Δ9-THC concentration reduced to 21.3% with generation of 43.2% Δ10-THC, 27.2% Δ6a10a-THC, 5.20% CBN, and 1.0% Δ8-THC. 40 minutes after the catalyst was introduced at 200° C., Δ9-THC concentration reduced to 12.2% with generation of 51.1% Δ10-THC 23.4% Δ6a10a-THC, 6.2% CBN, and 1.1% Δ8-THC. 60 minutes after the catalyst was introduced at 200° C., Δ9-THC concentration reduced to 9.3% with generation of 55.5% Δ10-THC 20.3% Δ6a10a-THC, 6.90% CBN, and 1.2% Δ8-THC. 60 minutes after the catalyst was introduced at 200° C., the mixture was heated to 220° C. to investigate effect of higher heat. After 20 minutes ramping to 220° C., Δ9-THC concentration reduced to 8.1% with generation of 55.5% Δ10-THC, 17% Δ6a10a-THC, 7.0% CBN, and 1.2% Δ8-THC. After 20 minutes at 220° C., Δ9-THC concentration reduced to 6.1% with generation of 58.3% Δ10-THC, 14% Δ6a10a-THC, 8.1% CBN, and 1.2% Δ8-THC. The mixture was then cooled under nitrogen. Reversed-phase or normal-phase chromatography may be used to further purify Δ10-THC over 80% (Δ10-THC 85%, Δ6a10a-THC 14%). Another method of achieving high purity is through recrystallization of Δ10-THC in organic solvents, which may raise Δ10-THC purity above 90%.

Example 4: Conversion of Δ9-THC to Δ10-THC in Low THC Material (Notebook B01-58.1)

The fourth example displays the General Reaction 1 and General Reaction 2 along with Side Reaction 4, 5, and 6 taking place, due to addition of excess catalyst. Additionally, higher temperatures than Example 3 was used in order to encourage General Reactions to complete, reducing Δ9-THC concentration below 0.30% although Δ9-THC concentration, catalyst concentration, and temperature may vary. Low vacuum (400,000 micron) was used in order to minimize Side Reactions 1, 2, and 3. A ratio of 30.4 grams of THC-sparse oil (4.1% Δ9-THC, 0.8% CBN, 56% CBD) to 0.2 grams (6.25 mmol) elemental sulfur pellets was used. In this example, the catalyst was added at room temperature and mixture was heated to 220° C. The mixture was heated under low vacuum for 1 hour. After 20 minutes under heat, Δ9-THC concentration reduced to non-detect with final concentrations of 1.4% Δ10-THC, 0.3% Δ6a10a-THC, and 3.0% CBN while maintaining original CBD content of 55.3% CBD. The increased temperature maintains the rate of the General Reaction until completion (Δ9-THC concentration is less than 30 mg/g) in less than 1 hour.

Example 5: Conversion of High Concentration Δ9-THC to Low Concentrations of Δ10-THC, Δ6a10a-THC, and CBN, while Maintaining Majority of Δ9-THC The fifth example slows the General Reaction 1 and General Reaction 2 by removing catalyst and oxygen while using medium vacuum (1 micron to 50 micron) to control Side Reactions 1, 2, 3, and using zero catalyst in order to prevent reactions 4, 5, and 6. General reaction was performed during a distillation of 2500 g of crude material containing 64.5% Δ9-THC, at 4 micron during cannabinoid distillation, and a temperature of 183-215° C. for 2 hours although cannabinoid concentration, temperature, atmospheric conditions and time may vary. After distillation, mass recovered was 1608 g and Δ9-THC concentration was 85.3% with generation of 3.1% Δ10-THC 0.80% Δ6a10a-THC, and 1.2% CBN.

Example 6: Conversion of Δ9-THCv to Δ10-THCv, Δ6a10a-THCv, and CBNv

The sixth example displays the General Reaction 1 and General Reaction 2 using Δ9-THCv as the starting material and uses nitrogen to minimize Side Reactions 1, 2, and 3 which generate excess CBNv. Additionally, minimal sulfur was used in order to minimize Side Reactions 4, 5, and 6, which reduce concentration of Δ10-THCv and Δ6a10a-THCv. Higher temperature than Example 2 was specifically used in order to increase the rate of General Reaction 1, generating a higher concentration of Δ10-THCv, although Δ6a10a-THCv may decrease due to degradation. 1 gram of high THCv oil (27.2% THCv) was added to mixture. In this example, the mixture was heated to 200° C. under nitrogen and then 0.01 g catalyst was added. The mixture was heated under nitrogen for 20 minutes. 5 minutes after, the catalyst was introduced at 200° C., Δ9-THCv concentration reduced to 13.1% with generation of peaks attributable to Δ10-THCv, Δ6a10a-THCv, and CBNv. Standards must be created in order to quantify these peaks.

The invention claimed is:

1. A process for the conversion of Δ9-THC to Δ10-THC, Δ6a10a-THC, and CBN.

2. The process according to claim 1 where the reactants are heated to a temperature between 163° C. to 225° C.

3. The process according to claim 1, where a catalyst and heat are added to Δ9-THC present in intact plant material.

4. A process for the conversion of Δ9-THC to Δ10-THC, Δ6a10a-THC, and CBN, comprising combining an oil containing THC and a catalyst under heat.

5. The process according to claim 4 where the catalyst is elemental sulfur or a Lewis base.

6. The process according to claim 5 where the ratio of moles of Δ9-THC to moles of sulfur in the mixture is between 1 mole Δ9-THC to 0.001 mole sulfur and 1 mole Δ9-THC to 2 mole sulfur.

7. The process according to claim 6 where the reaction mixture is heated and cooled under the atmosphere of an inert gas.

8. The process according to claim 6 where the reaction mixture is heated and cooled under atmospheric conditions.

9. The process according to claim 6 where the reaction mixture is heated and cooled under vacuum conditions.

10. The process according to claim 7 where the reaction mixture is heated to a temperature above 125° C. and below 300° C.

11. The process according to claim 7 where the reaction mixture is heated to 250° C. or above.

12. The process according to claim 8 where the reaction mixture is heated to a temperature above 125° C. and below 300° C.

13. The process according to claim 8 where the reaction mixture is heated to 250° C. or above.

14. The process according to claim 9 where the reaction mixture is heated to a temperature above 125° C. and below 300° C.

15. The process according to claim 9 where the reaction mixture is heated to 250° C. or above.

16. A process for the conversion of Δ10-THC to Δ6a10a-THC without a solvent.

17. A process for the conversion of Δ10-THC to CBN.

18. A process for the conversion of Δ6a10a-THC to CBN.

19. A process for the conversion of Δ9-THCv to Δ10-THCv, Δ6a10a-THCv, and CBNv.

* * * * *